US006246912B1

(12) United States Patent
Sluijter et al.

(10) Patent No.: US 6,246,912 B1
(45) Date of Patent: *Jun. 12, 2001

(54) MODULATED HIGH FREQUENCY TISSUE MODIFICATION

(75) Inventors: Menno E. Sluijter, Amsterdam (NL); William J. Rittman, III, Lynnfield; Eric R. Cosman, Belmont, both of MA (US)

(73) Assignee: Sherwood Services AG, Schaffhausen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/356,669

(22) Filed: Jul. 19, 1999

Related U.S. Application Data

(63) Continuation-in-part of application No. 08/671,927, filed on Jun. 27, 1996, now Pat. No. 5,983,141.

(51) Int. Cl.[7] ........................................................ A61F 2/00
(52) U.S. Cl. ............................................................ 607/100
(58) Field of Search ............................... 607/89, 99–102, 607/113, 148; 600/373, 547, 549; 606/34, 41

(56) References Cited

U.S. PATENT DOCUMENTS

| Re. 33,420 | 11/1990 | Sussman et al. . | |
|---|---|---|---|
| 4,565,200 | 1/1986 | Cosman . | |
| 4,735,204 | 4/1988 | Sussman et al. . | |
| 4,907,589 | 3/1990 | Cosman ........................... | 607/113 X |
| 5,233,515 | 8/1993 | Cosman ........................... | 600/301 X |
| 5,342,409 | 8/1994 | Mullett . | |
| 5,370,672 | 12/1994 | Fowler et al. . | |
| 5,417,719 | 5/1995 | Hull et al. . | |
| 5,433,739 | 7/1995 | Sluijter et al. .................... | 607/113 X |
| 5,478,303 | 12/1995 | Foley-Nolan et al. . | |
| 5,569,242 | 10/1996 | Lax et al. . | |
| 5,571,147 | 11/1996 | Sluijter et al. . | |
| 5,643,330 | 7/1997 | Holsheimer et al. . | |
| 5,658,322 | 8/1997 | Fleming . | |
| 5,690,692 | 11/1997 | Fleming . | |
| 5,702,429 | 12/1997 | King . | |
| 5,814,092 | 9/1998 | King . | |
| 5,908,444 | 6/1999 | Azure . | |
| 5,913,882 | 6/1999 | King . | |
| 5,925,070 | 7/1999 | King et al. . | |
| 5,938,690 | 8/1999 | Law et al. . | |
| 5,948,007 | 9/1999 | Starkebaum et al. . | |
| 5,951,546 | 9/1999 | Lorentzen ......................... | 606/41 |
| 5,983,141 | * 11/1999 | Sluijter et al. ...................... | 607/100 |

* cited by examiner

Primary Examiner—Angela D. Sykes
Assistant Examiner—Ryan Carter (57) ABSTRACT

A method and apparatus are provided for altering a function of tissue in a patient. An electromagnetic signal generated by a signal generator is applied to the tissue to be altered through an electrode. The electromagnetic signal has at least one frequency component above the physiologic stimulation frequency range at an intensity sufficient to produce an alteration of the tissue and a waveform that inhibits temperature elevation to the lethal temperature range of the tissue. Both externally coupled and fully implanted electrode and signal generator systems can be used at tissue sites in various parts of the body.

46 Claims, 7 Drawing Sheets

MODULATED HIGH FREQUENCY TISSUE MODIFICATION

RELATED APPLICATION

This application is a continuation-in-part of application Ser. No. 08/671,927, now U.S. Pat No. 5,983,141,filed on Jun. 27, 1996, entitled "METHOD AND APPARATUS FOR ALTERING NEURAL TISSUE FUNCTION."

FIELD OF THE INVENTION

The present invention relates generally to medical systems and procedures for prolonging or improving human life. More particularly, this invention relates to an improved method and apparatus for modifying the function or characteristics of neural and other tissue by applying pulsed or modulated high frequency electromagnetic fields to the tissue.

BACKGROUND OF THE INVENTION

The use of radiofrequency (RF) generators with electrodes applied near or in neural tissue for pain relief or functional modification is well known. For instance, the RFG-3C RF Lesion Generator available from Radionics, Inc., Burlington, Mass. can be used with electrodes placed near neural tissue to heat the tissue by RF resistive power dissipation of the generator power in the tissue. Thermal monitoring by a thermo sensor in the electrode is used to control the process. Heat lesions produced at tissue temperatures of 60 to 95 degrees Celsius (° C.) are common. Tissue dies by heating at about 45 to 50° C., so heat lesion generation is designed to elevate the neural tissue above this lethal temperature threshold. Often, the procedure of heating above 45 to 50° C. causes severe pain to the patient, which is so unpleasant (and frequently unbearable) that a local or general anesthetic is required during the heat procedure. Use of anesthesia poses a degree of undesired risk to the patient, and the destructive nature of and unpleasant side effects of the RF heat lesion are limitations of this technique.

Heat lesion generators typically use continuous wave RF generators with radiofrequencies of between 100 KiloHertz to several MegaHertz (viz. the RF generators of Radionics, Fischer, OWL, Elekta, Medtronic, Osypka, EPT companies). The theory and use of RF lesion generators and electrodes for pain and functional disorders is described in various papers (see, e.g., (1) Cosman, et al. "Theoretical Aspects of Radiofrequency Lesions and the Dorsal Root Entry Zone," *Neurosurg* 15:945–950, 1984; and (2) Cosman E R and Cosman B J. "Methods of Making Nervous System Lesions," in Wilkins R H, Rengachary S S (eds): *Neurosurgeny*. New York, McGraw-Hill, Vol. III, 2490–2498, 1984).

Neural stimulation is also now a common method of pain therapy. Stimulus generators with outputs of 0 to 10 volts (or zero to several milliamperes of current are used) are typical. A variety of waveforms and pulse trains in the "physiologic" frequency ranges of 0 to about 300 Hertz is also typical. This output is delivered to electrodes placed near or in neural tissue on a temporary basis (acute electrode placement) or permanent basis (chronic electrode implants). Such stimulation can relieve pain, modify neural function, and treat movement disorders. Typically, the stimulation is sustained to have a long-term effect, i.e., usually when the stimulus is turned off, pain will return or the therapeutic neural modification will cease after a short time (hours or days). Thus permanent implant electrodes and stimulators (battery or induction driven) is standard practice (e.g., the commercial systems by Medtronic, Inc., Minneapolis, Minnesota), and the stimulus is usually sustained or repeated on an essentially continuous basis for years to suppress pain or to treat movement disorders (viz. Parkinsonism, bladder control, spasticity, etc.). Stimulators deliver regular pulse trains or repetitive bursts of pulses in the range of 0 to 200 Hertz (a physiologic range similar to the body's neural frequency pulse rates), so this method simulates or inhibits neural function at relatively low frequency. It does not seek to heat the neural tissue for destructive purposes as in the high frequency technique. Chronically or permanently implanted stimulators often require battery changes, long-term maintenance and patient follow-up, which are expensive and inconvenient, often requiring repeated surgery.

Electrosurgical generators have been commonly used for decades for cutting and coagulating tissue in surgery. They typically have a high frequency, high power generator connected to an electrode that delivers a high power output to explode tissue for tissue cutting and to cook, sear, and coagulate tissue to stop bleeding. Examples of such generators are the generators of Codman, Inc., Randolph Mass., Valley Labs, Inc., Boulder, Colo., and EMC Industries, Montrouge, France. Such generators have high frequency output waveforms that are either continuous waves or interrupted or modulated waves with power controls and duty cycles at high levels so that tissue at the electrode is shattered and macroscopically separated (in cutting mode) or heated to very high temperatures, often above cell boiling (100° C) and charring levels (in coagulation or cauterizing mode). The purpose of electrosurgery generators is surgical, not therapeutic, and accordingly their output controls, power range, duty cycle, waveforms, and monitoring is not designed for gentle, therapeutic, neuro-modulating, sub-lethal temperature application. Use of an electrosurgical unit requires local or general anesthesia because of its violent and high-temperature effect on tissues.

SUMMARY OF THE INVENTION

The present invention is directed to a method and apparatus (a modulated high frequency signal generation apparatus in conjunction with a signal applicator, e.g., an electrode or conductive plate or other structure applied to the body) for modifying neural function of a patient's tissue. The inventive apparatus and method are functionally different from and have advantages over the RF heat lesioning systems, the stimulation systems, and electrosurgical systems previously described. Pain relief or neural modification, for instance, can be achieved by the inventive system without average heating of tissue above 45 to 50° C., without stimulating at frequencies in the range of 0 to about 300 Hertz and without burning or cauterizing tissue. Thus, as one advantage of the present invention, painful RF lesioning episodes at high lesion temperatures can be avoided and the need for chronic stimulation can be circumvented.

For example, by using an RF waveform output connected to an electrode inserted into the body near or in neural tissue, and by interrupting the RF waveform with bursts of RF power with interposed periods of off-time, a pain relieving effect or other neural modulating effect is accomplished, but the tissue temperature does not on average exceed approximately 45° C. This avoids painful heat lesions and potential side effects associated with the typical RF heat lesions, which involve tissue temperatures at a region near the electrode of substantially greater than 45° C. The modulated RF system can be used painlessly and easily, avoiding usual discomforts of standard RF heating procedures, yet relief of the pain or the neural dysfunction (such as, e.g., motor dysfunction, epilepsy spasticity, Parkinsonism, tremors, mood disorders, incontinence, etc.) can be long lasting using the novel system of the present invention, giving results in many cases that are comparable to those of RF heat lesions done at much higher temperatures. Another advantage of the modulated high frequency procedure is that it avoids the unwanted and sometimes harmful side effects of heat lesions, such as sensory or motor loss and can be performed on neural structures such as the dorsal root ganglion, in which making a heat lesion would not be recommended because of the delicate nature of that structure. Some applications of this invention include relief of back, head, and facial pain by procedures such as dorsal root ganglion or trigeminal ganglion treatments, spinal cord application for relief of intractable pain, spasticity, or motor control, treatment of the basal ganglia in the brain for relief of Parkinsonism, loss of motor control, tremors, or intractable pain. This pain relief or control or elimination of motor or other neural dysfunction can be comparable if not more effective than long-term stimulators with implanted electrodes, thus providing an alternative to avoiding the need for permanent stimulator implants, expensive implanted devices and circuits, battery changes, involving repeated surgery and expense, and repeated application of stimulation energy over long periods (months and years). The pain relief or neural modification can be accomplished by the present invention in a non-violent, painless way, avoiding average tissue temperature elevations into the lethal range and violent microscopic tissue separations, and thus the present invention is opposite to the objectives, systems, and methods involved in electrosurgical systems.

The pulsed or modulated high frequency technique can be applied to muscle tissue, joint tissue, neural structures in various organs including the central nervous system, the spinal cord, nerve roots, peripheral nerves, nerves and muscles in the heart, nerves and other tissues in the joints, and nerves in the teeth and jaws. For example, it can be applied to the heart to treat cardiac arrhythmias such as the Wolff-Parkinson-White (WPW) syndrome or to modify neural or muscular function of the heart. It can be used to modify nerve tracts in the spinal cord for neuropathic pain and spasticity, or in the spinal cord nerves proximate to the epidural space to relieve neurogernic pain. In addition, it can be used in the jaw, dental nerves, gums, trans-maxillary joint (TMJ) to relieve tooth pain, or maxilar joint pain. It can also be used in the joints between bones including elbow, shoulder, hip, spine, knee, foot, etc. to relieve pain and other functional disorder syndromes associated with those regions.

BRIEF DESCRIPTION OF THE DRAWINGS

For a fuller understanding of the nature of the objects of the present invention, reference should be made to the following detailed description taken in connection with the accompanying drawings wherein.

DETAILED DESCRIPTION OF THE INVENTION

Figure 1:
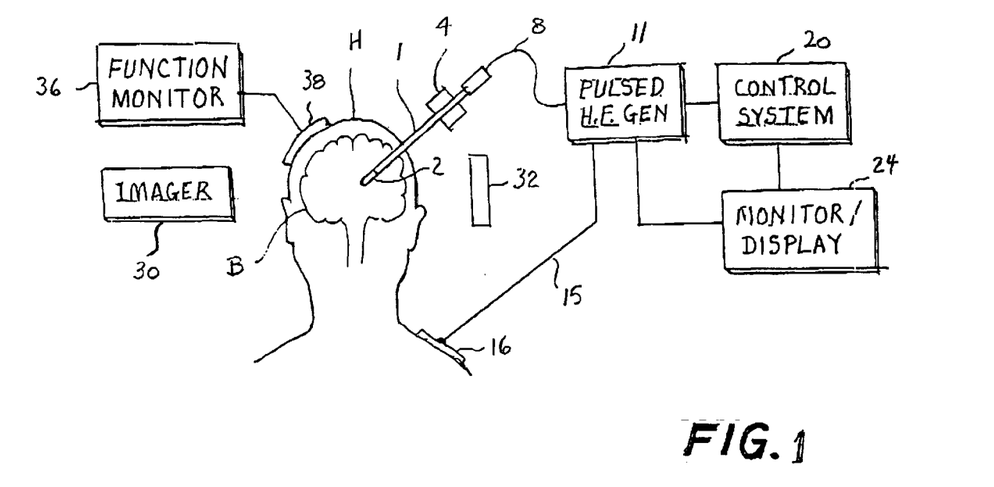
FIG. 1 shows a stereotactically directed brain electrode for delivering pulsed high frequency generator output to the brain of a patient with control and monitor functions in accordance with the present invention.

FIG. 1 shows one embodiment of a system and procedure according to the present invention involving an electrode applicator 1, which is inserted preferably by a stereotactic guide apparatus 4 into the brain B of a patient. An exposed electrode tip 2 is raised to an output voltage from a pulsed high frequency generator 11 that is connected to the electrode tip 2 via the electrode shaft 1 and the cable connection 8. The pulsed high frequency generator 11 generates a voltage output with a modulated high frequency waveform in accordance with the present invention. Examples of modulated high frequency waveforms are shown in FIGS. 12–15. For example, the output waveform may be modulated radiofrequency waves that have bursts of radiofrequency output and intermixed periods of zero or very low voltage output so that the electromagnetic field effects or electric field effects corresponding to the high frequency output on the brain tissue will result in neural modification according to the present invention. Such neural modification can take place using the modulated high frequency field around the electrode tip 2 without heating the brain tissue to lethal thermal temperatures. Various high frequency waveforms are suitable to achieve this non-thermally lethal, neural modification effect in accordance with the present invention. The electrode tip may include a temperature sensor, which is measured by a monitoring system 24 in association with the pulse generator 11. A control system 20 can vary the output of the pulse generator to the electrode tip 2 to achieve a desired clinical effect or end point.

As a specific example of an embodiment such as shown in FIG. 1, a brain electrode 1, having a rigid metal tubular shaft of one to several millimeters in diameter, can be inserted into the brain using a stereotactic frame apparatus 4 (an example of which is the CRW Stereotactic System of Radionics, Inc.). The electrode tip 2 may be placed at various functional targets within the brain, such as the thalamus, pallidum, sub-thalamic nucleus, singulum, or epilogenic centers. Application of the high frequency modulated output from generator 11 to the electrode tip causes neural modification of these functional neural structures within the brain to achieve a therapeutic effect. For example, if the electrode is placed in the thalamus, pallidum, or sub-thalamic nucleus, neural modifications may be induced to relieve the effects of tremor or Parkinson's disease. For example, the peak high voltage level of the high frequency generator output may achieve one to several tens of volts, while maintaining the tissue temperature near the electrode tip 2 at non-lethal levels corresponding to temperatures of the tissue less than approximately 45 to 50° C. Application of such voltage output for several seconds or minutes may result in neural modification of the tissue in the brain. Achieving the proper end point of the modification may be manifest in one example by cessation of tremor in the patient as the procedure continues. In other instances, functional monitors such as cortical electrode monitoring or EEG monitoring, as illustrated by applicator 38 and electrical output detector 36, may give indication of the proper effect or end point of the neural modification procedure.

Various imaging devices, illustrated schematically by element 30 and detector 32, may be used to confirm electrode position or other characteristics associated with the tissue during the procedure. Examples of imaging devices are CT scanners, MRI scanners, ultrasound scanners, X-ray and fluoroscopic devices, MMG magneto-encephalography devices, etc.

In a "monopolar" configuration, a ground reference pad 16 may be connected to the high frequency generator 11 to complete an electrical circuit through the patient's body.

Examples of disease states treatable by the embodiment of FIG. 1 are Parkinson's Disease, essential tremor, epilepsy, mood disorders, headaches, psychological diseases, spasticity, neuropathic pain, movement disorders, Alzheimer's Disease, and other various neurological diseases. The electric or electromagnetic fields emanating in the region of tip 2 caused by the pulsed high frequency voltage on the electrode tip 2 causes modification of the neural cells or neural cell structures such as modification of the cell membrane, DNA and RNA in the cell, cell body, cell nucleus, cell axon and action of unmyelinated or myelinated cell membranes, and can cause other changes on a macrocellular or molecular level within the brain cells.

Figure 2:
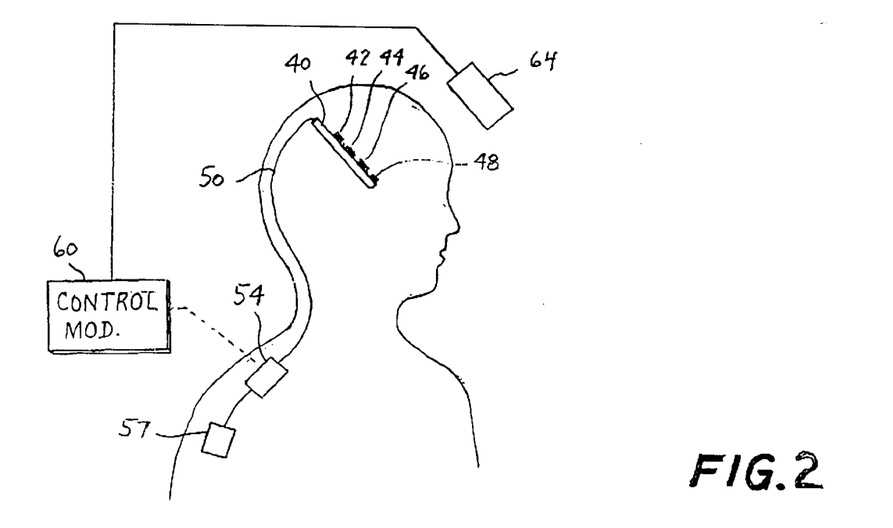
FIG. 2 shows a fully implanted high frequency generator connected to a deep brain, multi-contact electrode in accordance with another embodiment of the invention.

FIG. 2 shows another system and method in accordance with the present invention involving a deep brain catheter or shaft type applicator 40 that has multiple electrode contacts illustrated by 42, 44, 46, and 48. A multi-connector cable 50 connects the individual electrical contacts to a high frequency modulated output generator 54, which is battery powered by battery 57. The high frequency pulsed or modulated generator 54 may be of a biocompatible and compact form to be implanted under the patient's skin to make the entire system of generator and electrode an implantable structure. Control of the output levels and waveforms of the modulated pulsed high frequency output can be carried out by telemetric information transmission from control module 60. By reference, examples of external control modules controlling implanted voltage generators is the deep brain stimulation electrode system of Medtronic, Inc.

In the example of FIG. 2, the generator 54 may generate multiple modulated high frequency outputs, which are distributed to the single or multiple electrode contacts 42, 44, 46, and 48 in the deep brain applicator 40. The applicator may be placed appropriately as e.g., by stereotactic guidance within the patient's brain so that the electrical contacts are in proximity to critical structures for which neuromodification is indicated. By application of the high frequency output to the electrical contacts at various positions in the brain, various clinical effects can be achieved. For example, application of the modulated high frequency output of a certain voltage on electrical contact 48 may have one effect, whereas application to others of the electrical contacts 42, 44, and 46 may have a different neural modification effect. Thus, a surgeon who implants and controls the system may select the one or more electrical contacts to deliver the high frequency generator output to various positions in the brain to achieve a given clinical effect. In one instance, in the treatment of Parkinson's Disease, such an applicator 40 may be implanted in the basal ganglia of the brain and the pulsed high frequency output may be distributed to the electrodes according to optimize therapeutic effect on the patient's Parkinson's symptoms such as tremor, rigidity, distonia, etc. The surgeon may change the distribution of modulated high frequency output to the electrode contacts by the external control device 60. The control module 60 may be coupled to detectors schematically illustrated as element 64 to detect brain waves, EEG's, MEG signals, or other indications of neural modifications.

Figure 3:
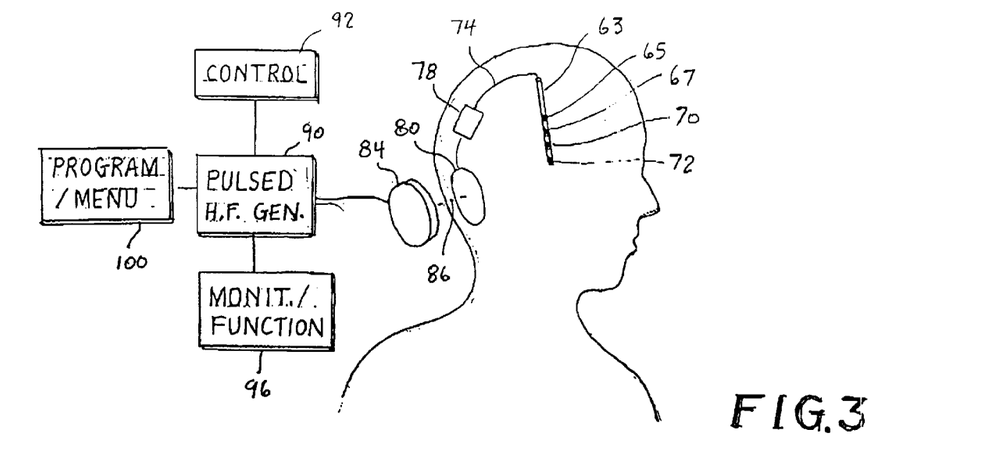
FIG. 3 shows an induction powered high frequency implanted generator connected to a deep brain, multi-contact electrode in accordance with another embodiment of the invention.

FIG. 3 shows a variation of the implanted, modulated high frequency waveform generator connected to a deep brain applicator 63 with multiple electrical output 65, 67, 70, and 72. The high frequency generator 70 is a fully implanted device and is connected to an induction coil 80, all of which are implanted under the patient's scalp. The electrode applicator 63 and its contacts are carefully placed in the desired positions in the brain in order to achieve a desired therapeutic effect. External to the body, a high frequency pulsed generator 90 is connected to an antenna or induction device 84. Device 84 is coupled electromagnetically to the pickup coil 80 within the patient's body so as to power the pulsed generator 78 when therapy via the electrode contacts is desired. A control device 92 may include variation of modulated high frequency output parameters such as voltage, duty cycle, waveform characteristic, etc. to achieve a desired therapeutic effect by controlling the output of generator 78. The pulsed generator may be programmed by a memory or a computer 100 so as to achieve various preplanned outputs of generator 78. A monitoring or imaging system 96 to check and control the neurological function of the patient, as in the example of spasticity, epilepsy, movement disorders, mood disorders, etc., may be cooperatively connected to the pulse generator 90 so as to achieve proper end points of the pulsed application or to turn on the generator output at appropriate times to grade or diminish the diseased state.

In one example of the embodiments of FIG. 3, the generator 78 may be a fully implanted microelectronic circuit that is capable of delivering an output waveform through the connection 74 to one or more of the electrode elements 65, 67, 70, and 72. The pickup coil 80 and its induction counterpart 84 outside the body may be used to change or control the parameters of the generator 78 output or to supply electromagnetic-induced power to the generator system by the external apparatus 90, 92, 96, and 100. The patient may manipulate the control function 90 himself to achieve the therapeutic effect when necessary, or this may be controlled by the clinician during periodic hospital visits to grade or titrate the effect of the neural modification in the brain to treat the patient's disease. An applicator such as 63 within the brain may be similar in dimensions to deep brain epilepsy electrodes made by Radionics, Inc. or to deep brain stimulating electrodes made by Medtronic, Inc. They may be constructed of polyurethane, polyethylene, silicone, etc., with connected, conductive elements such as 65 made from various materials like titanium, platinum, stainless steel, or other appropriate compositions for suitable biocompatibility and compatibility to image scanning such as CT, MRI, X-ray, etc.

The inductive coupling between transmission element 84 and receptor element 80 may take various forms. For example, 84 may comprise an electromagnetic coil that provides an electromagnetic signal, indicated by dashed line 86, representative of the output of a pulsed high frequency generator 90. The electromagnetic output field 86 from indicator element 84 may couple to the implanted coil 80 so as to induce an electromagnetic potential in the coil 80. The induced potential from 80 can be amplified by electronic unit 78 to deliver, through the connection cables indicated by 74, the appropriate programmed modulated output signals to one or a combination of the elements 65, 67, 70, and 72. The electromagnetic coupling 86 may be a source of power to energize the circuits in element 78. Alternatively, 78 may include batteries and pulse generation circuitry, and the electromagnetic coupling between 84 and 80 may be programmed by program/menu unit 100 so as to vary the signals or the output combinations to the electrode elements on applicator 63. The menu unit 100 may be preprogrammed or its program changed to effectuate different sequencing, voltage ranges, output waveform, a combination of stimulative and non-stimulative high frequency signals, etc. By reference, electromagnetic couplings between external apparatus and internally implanted stimulating devices is used by implanted deep brain stimulation (DBS) systems, e.g., those made by Medtronic, Inc.

In the example of FIG. 3, various doses of the modulated high frequency signal can be delivered to one or more of the elements on the applicator 63, implanted appropriately in the patient's brain. Variations of the signal output and distribution to electrodes can be tried and reprogrammed to determine the effect. Various sessions of pulsed high frequency output application can be carried out, and the effect on the patient monitored. The monitoring of patient function indicated by element 96 can be used as feed back to the pulse generator 90 and its control unit 92 to vary the applied output. Output can be applied by a clinician on repeated visits to his office or hospital site by the patient to suit clinical needs.

Figures 4, 5:
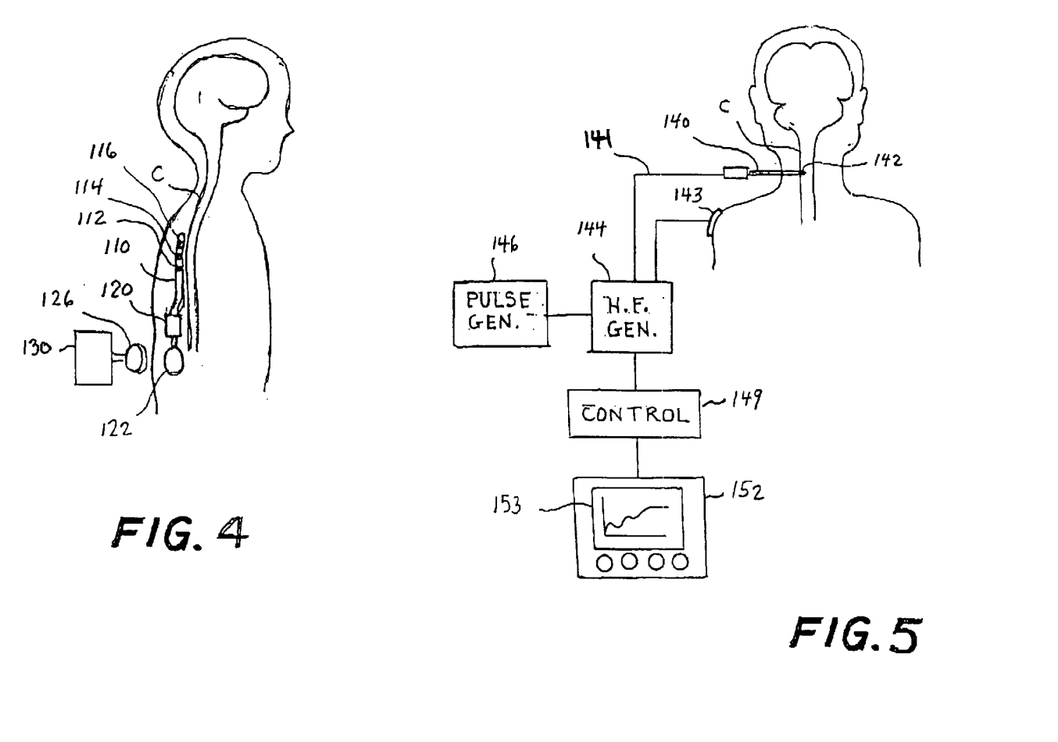
FIG. 4 shows an induction powered high frequency generator implanted for epidural spinal cord stimulation in accordance with another embodiment of the invention.
FIG. 5 shows a percutaneous electrode for application of high frequency modulated output to the spinal cord in accordance with another embodiment of the invention.

FIG. 4 shows an embodiment of the present invention in which a catheter-like applicator 110 with multiple electrode contacts, illustrated by 112, 114, and 116, is implanted near to the spinal cord C. The connections within the applicator 110 connect to a high frequency generator 120 that is also implanted in the patient. The generator produces modulated high frequency signals in accordance with the present invention. A coupling element 122 is implanted and connects to the generator 120. It is in electromagnetic communication to an external apparatus 130, which provides control, power or output generation through a transmitter element 126. Element 126 communicates via an electromagnetic field across the patient's intact skin to the pickup element 122. Element 130 may be a power generator or source of modulated high frequency signal. The signal may be sent to a transmitter coil 126 that in turn transmits by electromagnetic coupling to a pickup coil 122. The signal induced in the pickup coil then is transmitted to the implanted circuit element 120, which may appropriately apply to multiple leads within the catheter element 110 to connect to the electrode elements 112, 114, and 116. The element 120, therefore, may be an amplifying circuit, impedance coupling circuit, or other appropriate implanted circuit element so that the signal generated from the external apparatus 130 is appropriately applied to the applicator 110. Alternatively, element 120 may be a generator of the high frequency modulated signal. The electromagnetically coupled elements 126 and 122 may be a source of inducing power into the implanted system 122 and 120. In such an embodiment, the external generator 130 may be a power source generator to induce power to the implanted element 120 via the coupling elements 126 and 122. The internal circuit 120, therefore, generates the output signal applied to the applicator 110 and its electrodes. The element 120 may contain programmable elements that can be changed and modulated by the external system 130, which may comprise program, menu, monitoring control, and other functions as described in connection with the previous embodiments and figures.

FIG. 5 shows an embodiment in accordance with the invention that includes an electrode applicator 140 with an electrode tip 142 that can be employed percutaneously through the patient's intact skin to contact or penetrate the spinal cord C or its nerve roots, ganglia, and/or peripheral nerves. The electrode system 140 can be placed percutaneously within the spinal cord such that the electrode tip is within the various neural tracts within the cord, such as the spinal thalamic tract, dorsal root entry zone region, pyramidal tract, or other structures within the cord. Then the application of modulated high frequency signal output can be applied specifically to neural structures within the spinal cord. By way of example, electrodes that can be psercutaneously placed into the spinal cord are available from Radionics, Inc.

The electrode element 140 is connected by cable 141 to an external high frequency generator 144. The generator may be a power amplifier that amplifies signals from a pulse generator 146. The pulse generator 146 may provide modulated high frequency pulsed signal outputs in accordance with the present invention, and the generator 144 amplifies or, appropriately, modifies those signals for application to the electrode 140. A control system 149 may provide means for the operator to vary the parameters of the output signal or to monitor physiologic signals such as electrical activity monitored from the electrode tip 142 or to monitor impedance or thermal signals from the electrode. The electrode tip may include a thermal sensor such as thermocouple, thermistor, or other sensing means, and connections within the electrode 140 and cable 141 may be brought back to the control system 149 for monitoring temperature of the tissue near the tip 142. Graphic display element 152 may display the electrical output parameters from the high frequency generator in a two-dimensional or three-dimensional graphic representation on a screen 153. The monitor 152 may display the temperature signal registered from the electrode tip 142 or the impedance of the tissue surrounding the tip when imbedded in the cord or associated nerve roots, ganglia, etc. Electrical activity from the spinal cord or peripheral nerves may also be displayed on monitor 152 and used as feedback to the process of neural tissue modification in accordance with the present invention.

Applications of the embodiment in FIG. 5 may include percutaneous spinal thalamic tract modification where the electrode tip 142 is placed in the spinal thalamic tract. This may be used for neural modification in treatment of post-hepatic neuralgia, disaesthesia, central nervous pain, neuropathic pain, cancer pain, neurogenic pain, spasticity, or other central nervous system related syndromes. The electrode tip 142 may be placed in the dorsal or ventral roots or ganglia for treatment of pain and spasticity. Alternatively, the electrode tip 142 may be placed in the dorsal root entry zone or nucleus cordalis or other analogous structures for the treatment of herpes, phantom limb pain, intractable pain, sympathetic dystrophies, movement disorders, cancer pain, and other disease states. The electrode tip 142 may be placed near the sympathetic nerves or the nerve roots associated with the spinal cord in the treatment of pain, movement disorders, sympathetic dystrophies, herpes, or other clinical needs. The electrode tip 142 may be placed in neural structures within or peripheral to the spinal cord to moderate epilepsy, motor or sensory or pain diseases related, directly or indirectly, to these structures.

An electrode system for placement in the spinal cord, such as illustrated in FIG. 5, may have a stainless steel shaft 140 on the order of a fraction of a millimeter up to one millimeter or more. It may have a sharpened tip for penetration of the skin and the spinal cord. Shaft 140 may comprise an introduction needle through which the electrode tip 142 can be passed. By reference, example of composite introduction needles and electrodes is illustrated by the LCE Cordotomy Electrode Kit of Radionics, Inc. The electrode tip 142 may be permanently curved or may have a flexible side outlet or curved portion to achieve flexibility in directing the tip to different anatomical points in or near the spinal cord. By reference, examples of bent tip or flexible, curved tip electrodes are RFK Kit and SSE Electrode Kit of Radionics, Inc.

Figures 6, 7:
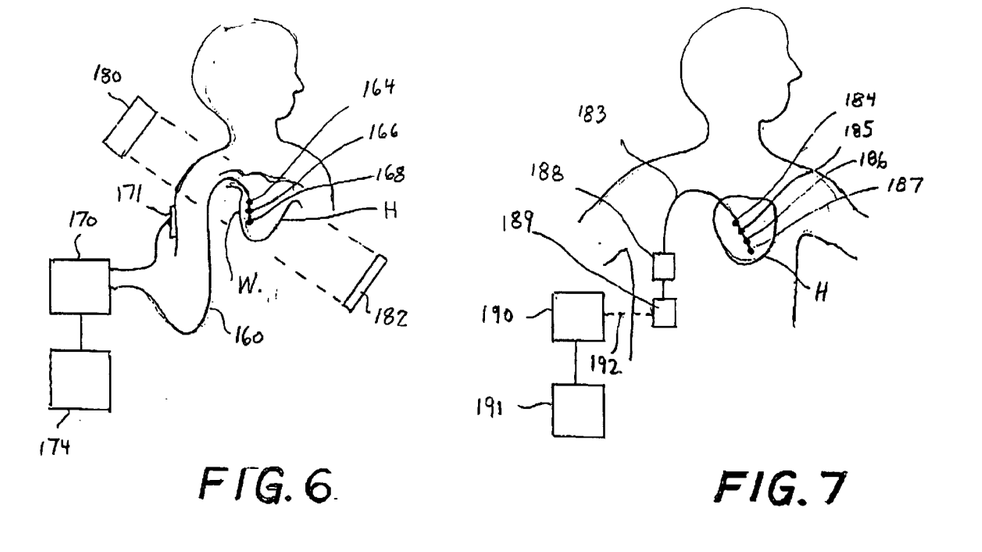
FIG. 6 shows a cardiac catheter placed in the heart of a patient for delivery of high frequency modulated output for treatment of arrhythmias or other heart conditions in accordance with another embodiment of the invention.
FIG. 7 shows an implanted cardiac high frequency generator connected to an implanted cardiac catheter for neural/muscular functional cardiac modification in accordance with another embodiment of the invention.

FIG. 6 illustrates another embodiment of the present invention in which a catheter-like applicator 160, having electrical contacts 164, 166, and 168 at its distal end, is placed into the body through, for example, a femoral artery such that the electrical contacts are located near the cardiac wall W in the heart H. The electrical contacts can be steered by steering mechanisms within the catheter element 160 to be placed against the nodes of the heart or against the muscle of the heart wall W where neural, muscular, or tissue modification is desired. The electrical tips or contacts 164, 166, and 168 are connected by wires within the catheter structure 160 to the output generator 170 that is external to the patient's body. The control monitor and/or signal generator units are illustrated by the block element 174. A reference electrode 171 can be used on the external surface of the patient's body as a return current sink for the output of generator 170. A modulated or pulsed high frequency signal from generator 170 can be applied to the catheter tip elements 164, 166, or 168 in a sequence or distributed array according to clinical needs. For example, neural or muscular modification may be desired on heart tissue of the wall W adjacent to one or more of the electrical contacts, and the application of the pulsed high frequency output to these contacts may result in a desired clinical effect. The effect can be monitored by monitor element 170, and different distribution of the output can be applied accordingly as needed. The modulated high frequency output can create fields and currents in and near the muscles and nerve cells and fibers of the heart thereby causing alteration of the functional behavior of the muscle or neural tissue as desired clinically. The fields and currents can cause modifications of the cell walls, internal structures, DNA, RNA, or other structures to cause temporary or more permanently-lasting functional effects on the nerve, muscle, or other tissue cells.

Also shown in FIG. 6 is a diagnostic imaging device 180 and detector system 182 to monitor the position of the electrical contacts in the heart prior, during, and after the procedure. Element 180 may be an X-ray, fluoroscopic, ultrasound, CT, MRI, PET, surface EEG, or other imaging, diagnostic, or monitoring device, which may or may not be in contact with the patient's body. In the case of MRI, it may be used to monitor the characteristic of the heart tissue during or after the procedure.

An example of an application of the catheter-like electrode system in FIG. 6 may be a flexible plastic catheter 160 of approximately 1 to 2 millimeter diameter inserted percutaneously through the femoral artery in the thigh and steered by internal steering mechanisms into the ventricle of the heart H. By reference, examples of flexible electrical catheters for radiofrequency cardiac ablation and mapping are provided by Medtronic, Inc. The electrical contacts such as 164, 166, or 168 can then be steered to the correct position in the heart where aberrant electrical signals exist. This can be determined by monitoring the electrical activity of the electrical contacts, which can be carried out by the monitoring function 174. This will enable proper positioning and targeting of the desired target tissue within the heart relative to the electrode tips. Once the proper positioning has been determined by this means, and possibly augmented by image monitoring of machine 180, a modulated high frequency output from generator 170 can be applied through the electrodes to the heart tissue so as to create the functional modification of the neural activity or the muscular activity of the heart according to clinical needs. Increasing the high frequency voltage or changing its frequency pattern may be desirable and actuated by the control element 174 through the generator 170.

An illustration of the application of such a neural or tissue modifying system and apparatus in accordance with the present invention may be alleviation of WPW syndrome, which causes dangerous cardiac arrhythmias. Heretofore, WPW syndrome has been treated with RF heat lesion techniques and flexible RF catheters placed in the heart. The heat lesion method creates an ablated region of tissue in the heart. An advantage of the present invention is that the pulsed high frequency application to catheter electrodes placed in the heart avoids the need for thermal destruction of tissue and therefore can avoid certain side effects of an RF heat ablation. Other applications could be the treatment of cardiac tachycardia or arrhythmias. The pulsed RF technique may also be used for treatment of infarction of heart tissue following heart attacks, heart injury, ischemia, or other diseases. Muscular or neural tissue modification can be effected by the pulsed RF technique when the electrodes are placed near the heart wall or impaled in the heart tissue near the affected region. As an alternative to the catheter-like electrode, a percutaneous, steerable, or rigid electrode placed through the chest wall into the heart for pulsed high frequency tissue modification may also be carried out.

FIG. 7 shows another embodiment of a pulsed high frequency tissuemodifying electrode 183, having electrical contacts 184, 185, 186, and 187. In this case, the electrical contact elements are connected through flexible cable or catheter 183 to element 188, which may be a pulse transmitter or a pulse generator as an intermediary to the pulse generator 190 located external to the body. The element 189 may be a receiving element to receive electromagnetic power or control signals, indicated by the dashed line 192 and emitted by the generator or transmitter element 190. Alternatively, element 189 may be an implanted battery system that powers a modulated high frequency pulse generator 188 that is also fully implanted in the patient's body. The element 190 in this embodiment may be an encoder for controlling the output of the generator 188 by means of coupling 192 across the patient's skin to a receiver element, also indicated in block 189. An external programming control or monitoring element 191 is shown connected to the transmitter 190 so that a clinician can change the pulse sequencing, pulse parameters, or modulation parameters associated with the output to the electrodes such as 184 through 187. In this embodiment, the electrodes, catheter applicator, and electronics are implanted in the patient and may be self-contained and battery powered, or may be modulated by external apparatus to suit clinical needs. By reference, examples of fully implantable battery-powered and telemetrically-controlled implanted cardiac stimulation devices are illustrated by the pacemaker and other systems of Medtronic, Inc.

Figure 8:
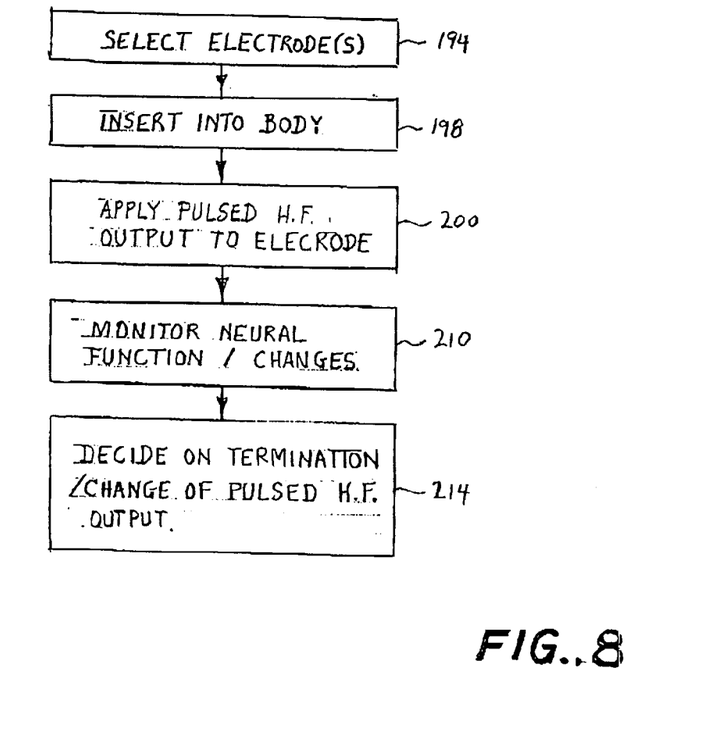
FIG. 8 is a flow chart illustrating operation of a pulsed high frequency signal application system in accordance with the invention.

Referring to FIG. 8, a flow chart is shown to illustrate the process of modulated high frequency tissue modification in conjugation with monitoring of function. The procedure starts by selecting one or more electrodes suitable for the clinical application (step 194). The electrode is inserted into the body (step 198), which may involve percutaneous placement, intraoperative placement, or full implantation, examples of which are given in the various embodiments described herein. The pulsed high frequency output from the high frequency generator is applied to the electrode, and the associated signal is delivered to the bodily tissue that is to experience functional modification (step 200). This step may include, alternatively, connection of cables or cords from the electrode to the high frequency generator, which may be located external to the body or may include connection of a fully implantable electrode applicator to a fully or partially implanted pulse generator, battery system, transmitter-receiver system, RF-coupled power source system, etc. The characteristic of the pulsed output of the generator may be changed or distributed to multiple electrode contacts in accordance with clinical need.

Before, during, or after application of the pulsed high frequency output, the tissue, neural structures, musculature activity and function, as well as any changes in that activity and function, may be monitored to ascertain the effect of the pulsed high frequency therapy (step 210). This step can include image scanning by CT, MR, X-ray, fluoroscope, ultrasound or other image means, electrical monitoring such as electrophysiologic electrical recording, evoked stimulation potential recording, monitoring of neural function, observation of patient movement, spasticity or other neural functionality, determination of achievement of pain relief, or relief of other muscular neurological or tissue/joint changes, etc. The clinician, ascertaining and monitoring such changes, can then decide on the continued course, modification of output parameters, repositioning of electrode position, changing of high frequency pulse, amplitude, duration, waveform, or termination of the procedure (step 214). A change in amplitude of pulsed application to the electrode may increase the effect required. Repositioning of the electrode may also be indicated according to monitoring data. Changes in the high frequency modulated pulse waveform, including changes in duty cycle, waveform shape, interruption cycles of the modulated pulsed high frequency signal, mixture of modulated high frequency signals above the physiologic stimulation range with signals within the stimulation or motor frequency range so as to create a mixed, hybrid, or other physiologic effect as desirable. Also in step 200 or step 210, monitoring of the temperature at various points in the electrode applicator or in the tissue near the region of pulsed high frequency application may be carried out so as to control the amount of power deposition involved in the procedure and to prevent or mediate the elevation of power deposition to the neural or muscular tissue to prevent exceeding the threshold for heat destruction and ablation.

Figure 9:
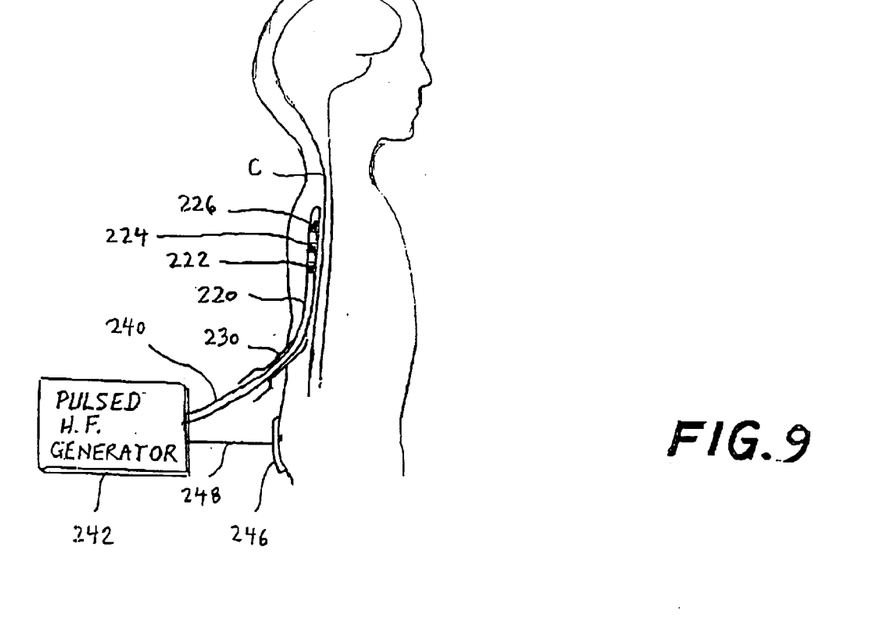
FIG. 9 shows an epidural catheter connected to a pulsed high frequency generator for neural modification of the spinal cord in accordance with another embodiment of the invention.

Referring to FIG. 9, another embodiment of the present invention includes an epidural catheter applicator 220 inserted so that electrical contacts 222, 224, and 226 are in proximity to the spinal cord C. The catheter may be inserted percutaneously by means of an insertion needle 230. By reference, use of insertion needles and epidural catheters is illustrated by the spinal cord stimulation instrumentation produced by Medtronic, Inc. The insertion guide needle may be, e.g., a Tuoy needle with curved or adapted tip and stylet to be percutaneously pushed through the skin near the epidural space. With removal of the stylet, the catheter structure 220 can be slid in such that the electrode contacts 222, 224, and 226 can be put into proximity of the spinal cord at a level corresponding to associated neurological disease. The catheter 240 is connected to the pulsed high frequency generator 242 and electrical connections within the catheter 240 connect to the electrical contacts such as 222. Output from the generator 242 therefore can be distributed, controlled, and monitored to the electrical contacts of the applicator 220. In addition, a reference electrode 246 is shown contacting the external skin of the patient and connected to the generator by cable 248 so as to produce a reference electrical contact. Alternatively, bipolar arrangements between two of the applicator electrodes such as, e.g., between elements 222 and 224 may be used to create a "bipolar" electrical configuration at the spinal cord itself. By reference, the published articles by Cosman, et al., referenced above, describe radiofrequency electrode tip configurations. The external apparatus 242 may comprise a high frequency pulsed or modulated high frequency generator in accordance with the present invention plus various control monitoring display and imaging accessories as described in connection with the above figures.

In a specific embodiment associated with FIG. 9, a catheter made of flexible material such as polyurethane may have a diameter of approximately 1 millimeter, and the electrical contacts such as 222 may be stainless steel, platinum, tungsten, or other tubular rings bonded to the substrate catheter 220 and connected by wires internal to the catheter to the external generator 242. The number of electrical elements such as 222 may vary from one to several, depending on the clinical need. Construction of the catheter may have reinforced metal spirals and be made of various bio-suitable materials. The length of the electrode elements, such as 222, may vary from a fraction of a millimeter to several millimeters according to the application. Application of the pulsed generator output to the spinal cord C through the electrode such as 222 may comprise elevating the maximum voltage of the pulsed output signal from around one volt to several tens of volts, and the time duration of application may range from seconds to several minutes, depending on the clinical effect desired. The applicator 220 may have temperature sensors in one or more positions of the contact elements 224 or at other positions along the length of the catheter to monitor heat deposition and prevent heat lesion and ablation effects.

Figure 10:
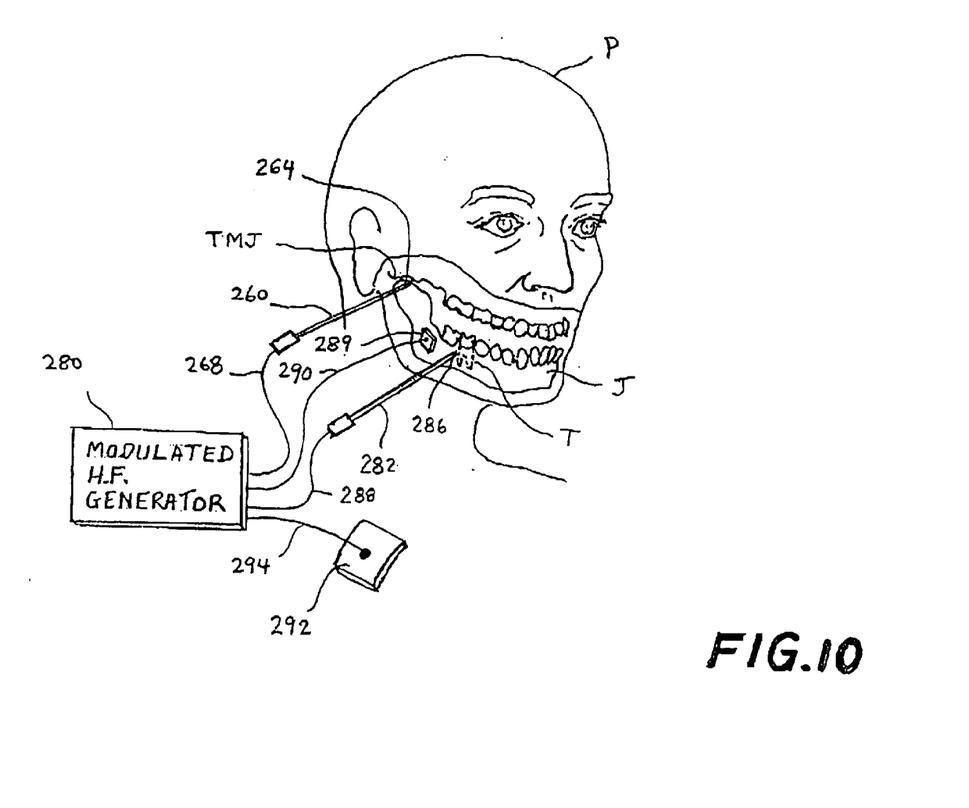
FIG. 10 shows electrode applicators for bony joint structures and dental structures for neural muscular modification in accordance with another embodiment of the invention.

Referring to FIG. 10, another application of the present invention is shown to mediate pain or other functional disorders for the teeth or in association with joints between bony structures in the body. A pointed electrode, illustrated by element 260, with an electrically conductive tip 264, may be inserted into or near a joint between bodily bones such as the trans-maxillary joint (TMJ). The electrode may or may not have sharpened tip or a guide insertion needle may or may not be used to help the insertion. The electrode may be flexible or curved to facilitate insertion or to curve around or between the joint to facilitate approximation to tissues to be treated. Joints can be the source of discomfort and pain, and this kind of pain can be relieved by application of pulsed or modulated high frequency through electrodes in accordance with the present invention.

As an example of relieving pain associated with abnormalities in joints, the electrode 260 with the sharpened, conductive tip 264 is inserted into the trans-maxillary joint TMJ. The electrode is electrically connected via cable 268 to the external generator 280. Generator output is a pulsed or modulated high frequency output in accordance with the present invention. Positioning the electrode tip 264 near the aberrant tissue near or in the joint and applying the output of generator 280, alleviation of pain and modification of pain-sensing neural structures can be effected. The electrode shaft 260 may be of small gauge, for example in the range of 1 millimeter or less in diameter, and comprise a rigid, metal tubing for percutaneous insertion. Also shown is a reference electrode 292, which is connected to the generator system 280 by cable 294 for a reference electrode contact.

In another application of the embodiment of FIG. 10, an electrode 282 with pointed or non-pointed, exposed conductive tip 286 is inserted near or in contact with the gums of the patient to alleviate dental pain. Again, the electrode is connected via cable 288 to the high frequency modulated output generator, and the electric field and currents associated with the generator output are applied near to the roots and nerves of the tooth so as to relieve dental or jaw pain during surgery or at other times.

Alternatively, in another embodiment of the invention in FIG. 10, the applicator could be in the configuration of a plate 289 put on the surface of a portion of the gums or on opposite sides of the jaws near the tooth, or on the tooth or tooth roots to produce a pain relieving effect. Electrode 289 is connected by cable 290 to generator 280 as for the other embodiments. Either percutaneous or transcutaneous application of modulated pulsed high frequency output, which is thereby applied to the nerves or roots T of a tooth or other points on the jaw J of the patient, can have the effect of pain relief.

A similar application of pain relief or neural or other tissue modification in accordance with the present invention can be devised by those skilled in the art. For example, insertion of an electrode applicator similar to that in FIG. 10 but in other joints and structures in the body can relieve related pain syndromes. For example, the joints of the arm, wrist, leg, feet, hip, or spine can be approached by percutaneous needle placement under image guidance such as fluoroscopy. Application of pulsed high frequency fields through the applicator can be used to relieve joint related pain syndromes.

Forms and embodiments of the system and method of neural or tissue function modification by pulsed or modulated high frequency fields can be devised to accommodate specific anatomical areas or neurological, muscular, or functional disorders. For example, electrodes inserted percutaneously in the urological system or near the prostate or in the gynecological region can be used to mediate incontinence, pain, movement dysfunction, or other neurologically related or muscular related abnormalities. Electrode applicators can be devised in many forms, shapes, and functions with various materials to accommodate particular applications. Application of modulated or pulsed high frequency field gradients, currents, voltages, waveforms, and signal outputs can have varied and therapeutic effect on nerves, axons, nerve cell bodies, neural structures, ganglia, central nervous system structures, brain neuronal structures, spinal cord tracts and structures, dorsal root entry zone structures, peripheral nerve and nerve root structures, muscle tissue, cancerous tissue, joint tissue, intravertebral disc tissue, periosteal bone tissue, and other cell types so as to cause modification of the function of the cells in a non-thermally lethal way so as to alter the function in a therapeutic manner in accordance with the present invention. Examples of syndromes that are affected have been given above and are not limited within the scope of this invention to movement disorders, pain, pain syndromes, central pain, peripheral pain, spasticity, epilepsy, mood disorders, brain functionality, muscle spasm, muscle pain, bladder, urinary, sexual, and bowel disorders, and other disease states related to cell function that can be modified by proximal electromagnetic and current field as delivered in the present invention.

Figure 11:
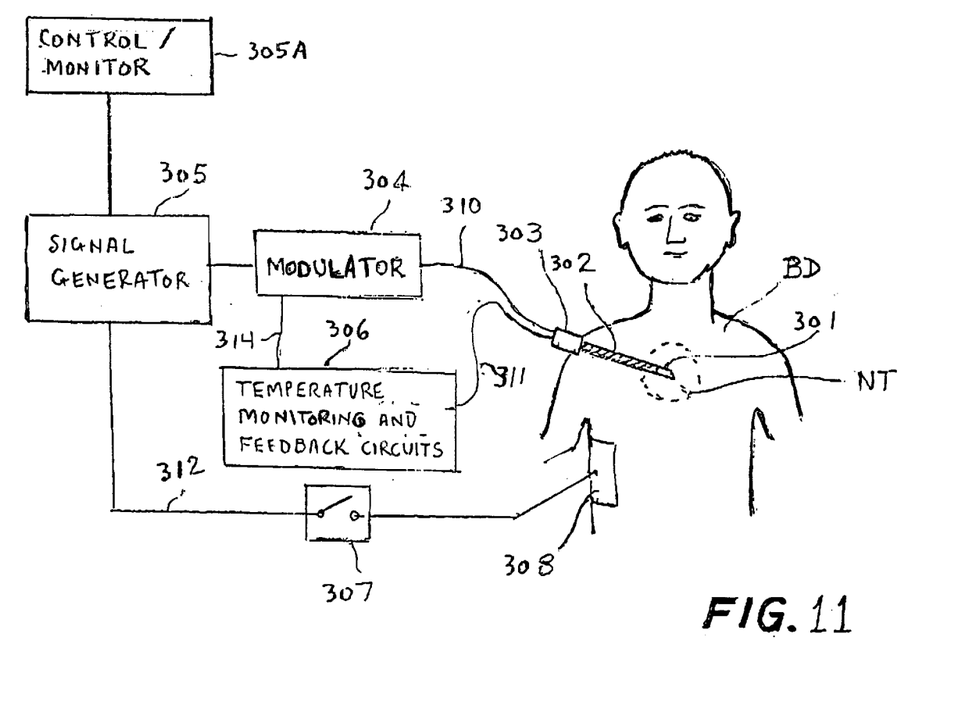
FIG. 11 is a block diagram showing elements of a system in accordance with another embodiment of the invention.

Referring to FIG. 11, another embodiment of the present invention is shown in block diagram and schematic elements. An electrode with uninsulated conductive surface 301 (for example a conductive tip end) is in proximity to a region of neural muscle or other tissue NT (viz. illustrated schematically by the dashed boundary). The electrode has an insulated shaft 302 and connection or hub portion 303, inside of which there can be electric connections to surface 301. The electrode 302 could be placed percutaneously, on the organ surface, surgically and so on, and placed in an organ desired to be treated. Connection 310 electrically connects to the surface 301 through the electrode shaft 302 and to electronic supply units 304 and 305 (which are shown outside the body, but which may be miniaturized and implanted inside the body). Element 305 is a signal generator of signal output (viz., voltage, current, or power), and element 304 is a modulator to modulate (for example the amplitude of) the high frequency output from 304. The electromagnetic output from 304 and 305 is connected to electrode surface 301, and therefore is conductively exposed to tissue NT. As an example, element 305 can take the form of an RF power source with a continuous wave output (viz. for example, similar to the model RFG-3C generator of Radionics, Inc.). Element 304 is a pulse modulation unit that switches on and off the RF output from 305 at a designed rate and duty cycle. RF output generators or supplies and modulation circuits are known in high frequency technique (e.g., *Radio Engineering* by Fredereck E. Terman, McGraw-Hill, New York, 1947, 3rd Edition). Further shown is a temperature monitoring element or circuit 306 which connects by cable 311 to the electrode and to a thermal sensor (viz. thermistor or thermocouple) inside the electrode applicator or conductive tip 301 to measure the temperature of the tissue NT near the tip. (Such thermal sensing circuits and electrodes are illustrated by the Model RFG-3C and associated thermal-sensing RF electrodes of Radionics, Inc.). Further, reference electrode 308 is shown in electric contact to the patient's body BD with connection wire 312 to generator 305 so as to provide a circuit for return current from electrode applicator 301 through the patient BD (such reference electrodes are common with RF lesion generators; see Cosman, et al., 1984). Element 307 is a switch or circuit breaker, which illustrates that such a return circuit could be opened to limit such direct return current, and limit such current to inductive or reactive current characteristic of time varying circuits such as RF circuits.

In operation, the voltage or current output from generator 305 and modulator 304 are impressed upon tissue NT, which may be neural tissue such as spinal nerves or roots, spinal cord, brain, etc. or other tissue such as muscle, ligaments, bone, periosteum, spinal discs, joints or joint tissues, and so on. In accordance with the present invention, such electromagnetic output can cause energy deposition, electric field effects, and/or electromagnetic field effects on the cells in the tissue NT so as to modify or destroy the function of such cells. For example, such modification of neural function may include reduction or elimination of pain syndromes (such as spinal facet, mechanical back pain, facial pain) in some cases, alleviating motor dysfunction, spasticity, Parkinsonism, etc., epilepsy or mood disorders. Because the RF output from 304 is modulated by element 305, its percent on-time is reduced so that sustained heating of tissue NT is reduced, yet the therapeutic effects of the impressed RF voltages and currents on the tissue NT are enough to produce, in the case of nervous or joint tissues, the pain reducing result. The generator 305 can have a power, voltage, or current output control 305A (as on the Radionics Model RFG-3C RF generator) to increase or decrease the output power magnitude or modulated duty cycle to prevent excessive heating of tissue NT or to grade the level of pain interruption as needed clinically. Output control 305A may be a knob that can raise or lower the output in a smooth, verniated way, or it can be an automatic power control with feedback circuits. In this regard, temperature monitor 306 can provide the operator with the average temperature of tissue NT near electrode tip 301 to interactively prevent temperatures near tip 301 to exceed the range of approximately 45° C. (on average thermally lethal to tissue NT), and thus to avoid is the higher temperature ranges for the usual heat lesioning procedures described above. For example, temperature monitor 306 may have feedback circuitry to change the modulation duty cycle (by, e.g., longer or shorter on-times) to hold the temperature near tissue NT to below a set value (viz. 40 to 45° C.), illustrated by the feedback line 314 in FIG. 11. In addition, the high frequency waveform from the generator 305 may or may not be free from substantial stimulative components in the 0 to about 300 to 400 Hertz range, which is lower than radiofrequencies. If the waveform is without stimulative frequencies, it will avoid the stimulation effects that are typical for stimulator system applications as described above.

Figure 12:
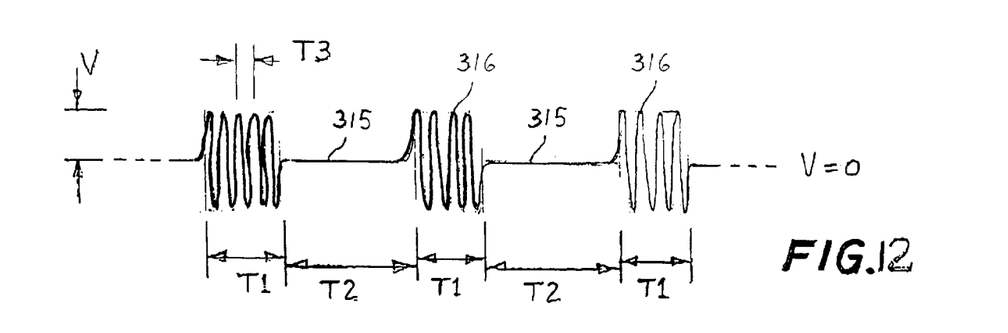
FIG. 12 is a graph of an interrupted RF waveform output from an RF generator in accordance with the invention.

As an example of a modulated RF waveform that accommodates the system of the present invention, FIG. 12 shows schematically a high frequency output of voltage amplitude V and of burst duration T1 between which on-time bursts there are illustrated periods of zero voltage of duration T2. During the on-time T1, the RF signal output is oscillatory with time period T3 between maximum voltages V. The reciprocal of T3 is proportional to the value of the radiofrequency (viz., 1 Mega Hertz RF output corresponds to T3=1 microsecond). This is an interrupted or bursting type of modulated high frequency waveform. During the high frequency on-time T1, the voltage can oscillate between plus and minus its maximum value V. Accordingly, an electric field is produced around the region of the electrode applicator (as for instance the exposed electrode tip 301 in FIG. 11). The electric field has a cell modifying, or pain-relieving, or neural-altering effect on the tissue near or among the nerve cells, nerve fibers, or other tissue cells. Pain relief and neural modification can accordingly be accomplished by this high frequency bursting voltage and accompanying electromagnetic field, and also accompanying current among the neural and other tissue cells. During the off period, there is minimal or no voltage (e.g., V=0 at the electrode applicator), and thus no electric field or electric currents in and among the neural tissue. During that period, no heat deposition is present. Thus, over the entire cycle, from on period T1 through off period T2, the energy deposition, on average, can be adjusted so that there is no excessive heating, on average, around the electrode applicator. Thus, the usual mechanism of continuous on-time high frequency voltage and current, as in previous heat lesion techniques, is avoided, and therefore the achievement of high average temperatures near or around the applicator tip may be limited by the present invention. The usual heat lesion process in which tissue temperatures, on average, exceed 45° can be avoided. In many instances, this avoidance of high temperature domains due to high average heat dissipation of the radiofrequency power will prevent acute pain of the process to the patient. By having the interrupted waveform, as in FIG. 12, the average power is thereby reduced and the average heating around the electrode tip or applicator is accordingly reduced. However, substantial voltages V (or currents) can still be sustained during the on period with their resulting therapeutic effect on the tissue. These waveforms may be applied for several seconds or minutes or long chronic or acute application as is clinically required.

To give a representative example of values for parameters in an interrupted high frequency waveform as in FIG. 12, the overall pattern of the waveform may have a total period of one second, meaning that the sum of T1+T2=1 second. The on period T1 can be 20 milliseconds, and the off period T2, therefore, can be 980 milliseconds. Voltages V in the range of 10 to 30 volts or more can be used. It can be used with a pain relieving effect in certain tissues. Average tip temperature around an electrode tip such as the exposed tip element 301 in FIG. 11 can be maintained at or below 40° C., well below thermo-lethal levels. Electrodes with diameters of 1 or 2 mm shaft (for example the shaft 302 of a cannula in FIG. 11), with an exposed tip of 1 to 10 mm (such as the tip element 301 in FIG. 11) can be used and the electrode can be inserted in around cell structures in the brain, peripheral nerves or peripheral nerve ganglia, or other tissue types to accomplish pain relief or other functional alteration. Variation of these parameters can be made with similar therapeutic effect, and various geometries of conductive electrode or applicator can be effective. Illustrations of a wide variety of such electrodes are illustrated by the product line of Radionics, Inc. Other examples are shown in the figures above. Pointed or sharpened electrodes (such as illustrated schematically by electrode tip 301 in FIG. 11) are useful for penetration of the electrode through the skin to the target tissue site, and electric or current fields of higher intensity will be present at a sharpened point for a given applied voltage (such as V in FIG. 12), which will be effective in altering neural or other cell function.

Figure 13:
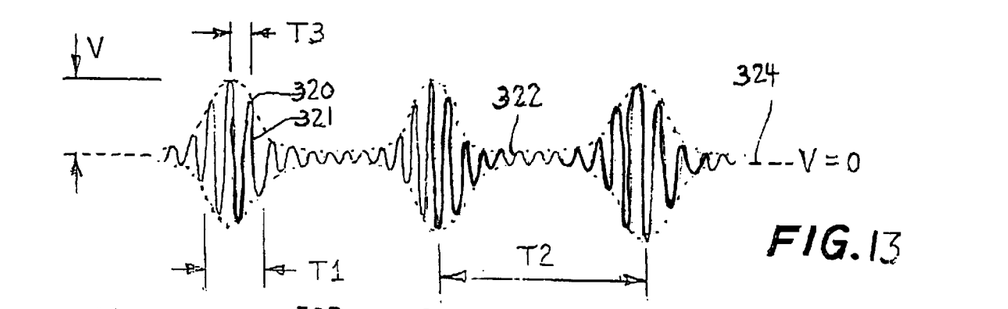
FIG. 13 is a graph of a modulated frequency waveform in accordance with the invention.

FIG. 13 shows a variation of a modulated high frequency waveform that accomplishes high peak voltage swings with reduced average power deposited in tissue. The baseline voltage may be put at zero (i.e., V=0), shown by dashed line 324. The solid line 321 represents the actual waveform, which has rapid oscillations at the radiofrequency and has an overall envelope, represented by dashed line 320, that has high points and low points with an approximate on time T1 and a time period between envelope of modulation maxima T2. T1, again, could be a percentage on time of 2 percent (as described above for 20 milliseconds on time out of 1 second total), and this on time T1 may vary considerably while still maintaining substantial off time so as to prevent overall average high temperature heating (as in the usual RF heat lesion systems). Such a modulation envelope (as dashed line 320) can be achieved by using a modulated signal generator that varies the input or output gain of a high frequency generator (as element 305 in FIG. 11) so as to achieve such a waveform as in FIG. 13. In such circuitry, which is commonly used in pulse generation techniques, low frequency filtering or selection of modulation parameters can avoid stimulation voltage or current components at the physiologic range of 0 to 300 Hertz so that unpleasant stimulative effects can be avoided during the therapeutic intermittent high frequency lesion process.

Figure 14:
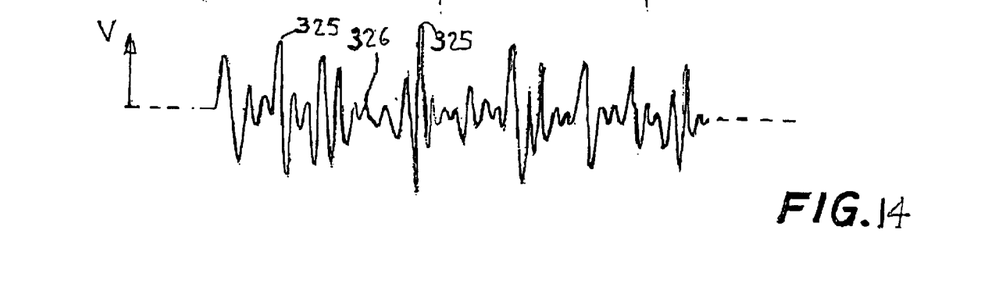
FIG. 14 is a graph of an irregular frequency waveform in accordance with the invention.

FIG. 14 shows yet another embodiment of an interrupted high frequency waveform in accordance with the present invention. Here there is a non-periodic variation of the voltage represented by the excursions of the voltage V represented by excursions on a vertical axis. The maxima point 325 can occur at random positions in time. The time difference between maxima can also vary in an irregular or even random way. This waveform may have no repeating or periodic structure but may be analogous to high frequency noise with random amplitudes, peaks, zero crossings, and carrier high frequencies. Such a waveform can be generated by random noise generators, spark gap signals, or other noisy signals that are known in the field of signal generation (viz. *Radio Engineering*, cited above). Filtering can be applied in the wave generator and power amplifier so that lower frequencies in the physiologic range will not be present to give undesirable stimulation effects.

Figure 15:
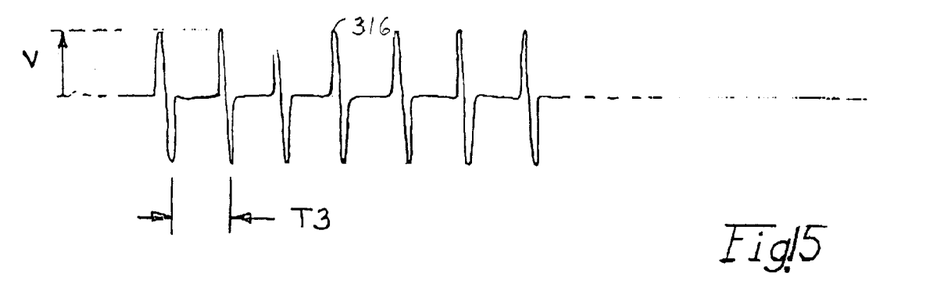
FIG. 15 is a graph of a repeated frequency waveform with a lowered output duty cycle in accordance with the invention.

FIG. 15 shows yet another possible high frequency waveform of interrupted, repeated bipolar pulses with a frequency above the physiologic stimulation frequency range (i.e., 0 to about 300 Hertz). The pulse on-time may be short enough so that the power deposition can be kept low enough to prevent heating, and yet the peak voltage V is sufficient to alter the neural function.

Variations of such waveforms are possible with the same intermittent high frequency effect for pain or neurological modification. For instance, instead of a baseline V=0, and a slowly varying baseline of non-zero value can be used. Also, the time average of the signal need not be zero. The on and off switching of a high frequency signal such as in FIG. 12 can be done at a non-periodic or non-regular, repeating rate so that, on average, the polarization effects in the tissue are still maintained at a low level. The average power deposition can still be maintained at a low level with non-periodic, interrupted high frequency waveforms. The high frequency carrier frequency (e.g., represented by the inverse of time T3 in FIG. 12 and FIG. 13) may also be non-constant. Varying or combined or superposed high frequency waveforms can be used as the carriers, and these combined or composite high frequency waveforms can be interrupted or modulated in accordance with the present system and invention. Pulse waveforms with high frequency carriers can be shaped in a variety of ways, e.g., with fast rising leading edges and slow or falling off or exponential trailing edges. The signal generator waveform can have a peak intensity that is much higher than the average or RMS intensity to yield a high electromagnetic field or current density on the neural tissue while maintaining the average power deposition in the tissue at a sufficiently low level to prevent heating above lethal tissue temperatures (viz. 40 to 50° C.).

Figure 16:
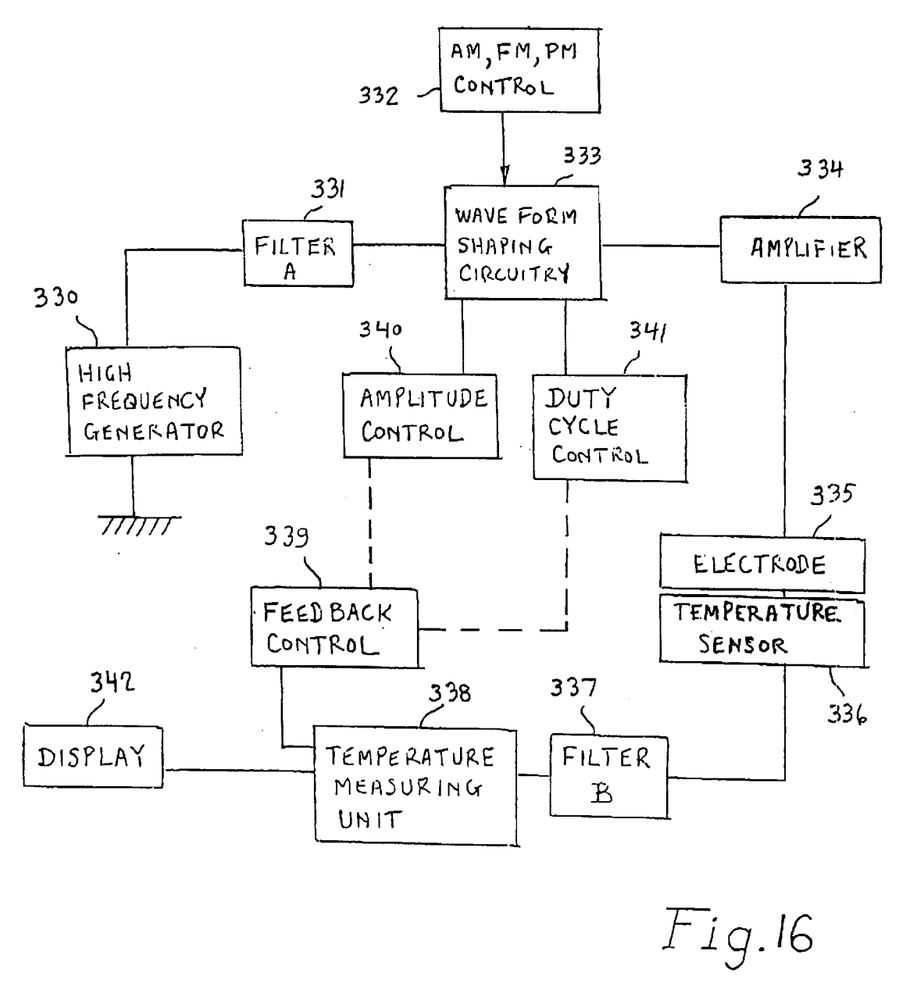
FIG. 16 is a block diagram showing elements of a system for generating modulated frequency signals in accordance with the invention.

FIG. 16 shows a block diagram of a system for generating modulated high frequency signals (similar but in more detail to the block element of high frequency generator 305 and modulator 304 of FIG. 11).

Element 330 represents a signal generator that can generate a high frequency signal of periodic or non-periodic frequency. This has input to element 331, which is a filter system that selectively filters out frequencies that could cause unpleasant, undesired, or damaging physiological signals. The signal is then fed into element 333, which is a waveform shaping circuit, and will shape the waveform input from element 332, which provides amplified modulation and./or frequency modulation and/or phase modulation control. Circuits of this type are described, for instance in *Radio Engineering* by Terman (cited above). Additional waveform shaping can be done by elements 340 and 341, which can control the amplitude of waveform and/or the duty cycle of the waveform, respectively. This resultant signal is then fed into a power amplifier represented of element 334. This is a wide band amplifier used to increase the signal to power levels appropriate for clinical use. This energy is then delivered to the patient via an electrode depicted as element 335.

A temperature sensor or plurality of temperature sensors, represented by element 336, can also be placed and connected in proximity to this electrode so as to insure that the temperature does not exceed desired limits. This temperature sensor signal is fed through element 337, which is a special filter module used to eliminate high frequency components, and thus not to contaminate the low-level temperature signals.

The temperature signal is fed to element 338, which is a standard temperature measuring unit that converts the temperature signal into a signal that can be used to display temperature and/or to control, in a feedback manner, either the amplitude and/or the duty cycle of the high frequency waveform. In this way, power delivery can be regulated to maintain a given set temperature. This flow is represented by element 339, which is a feedback control device. The dotted lines from element 339 to elements 340 and 341 represent a feedback connection that could either be electronic and/or mechanical. It could also simply be a person operating these controls manually, based on the visual display of temperature as, e.g., on a meter or graphic display readout 342.

As was explained with respect to the disclosed embodiments, many variations of circuit design, modulated high frequency waveforms, electrode applicators, electrode cannulas will be appreciated by those skilled in the art. For example, various electrodes or electrode applicators are possible, including electrodes with tubular shapes, electrodes with square shafts, flat electrodes, area electrodes, multiple electrodes, arrays of electrodes, electrodes with side outlets or side-issued tip electrodes with flexible tips that extend from an insertion cannula or needle to follow a curved path within tissue such as joints, spinal discs, muscle, etc., electrodes with broad or expandable or conformal tips, electrodes that can be implanted in or put in surface contact with various portions of the brain, spinal cord, interfecal space, interstitial or ventricular spaces, nerve ganglia, muscle, joints, skin, bone, etc. can be used in accordance with the present invention.

The frequency range for the so-called high frequency waveforms, as shown for instance in FIGS. 12–15 can be used over a wide range. For example, the "high frequency"

characteristic of 1/T3, which may be only one of many high frequency components, can be above the so-called physiologic stimulation frequency range of 0 to about 300 Hertz. This high frequency may also range up into the radiofrequency or microwave range (viz. 50 Kilo Hertz to many Mega Hertz).

The application time of the modulated high frequency signal may vary from seconds to several minutes to even hours or continuously depending on clinical needs and applications.

Mixtures of frequencies can be done as discussed above. These could be admixtures of "high frequencies" (above the physiologic stimulation range (of about 0 to 300 Hertz) and lower frequencies (within that stimulation range of about 0 to 300 Hertz). Thus one skilled in the art could have both modulated high frequency and stimulation frequencies for various clinical effects, such as stimulation blockage of pain while neural modification is being applied according to the present invention Modulated high frequency outputs applied to applicators may also be used to provide heating of the tissues near the applicator so that a combination of thermal effects and modulated field effects takes place on the tissues to be treated. This may have clinical utility in some cases. Intermittent or mixed applications on continuous and modulated high frequency outputs, high power modulated outputs, and stimulation outputs may be used to suit clinical needs and are intended to be within the scope of the present invention.

In view of these considerations, as would be apparent by persons skilled in the art, implementations and systems should be considered broadly and with reference to the claims set forth below:

What is claimed is:

1. A method of altering a function of tissue in a patient comprising:
   generating an amplitude modulated signal having at least one frequency component above a physiologic stimulation frequency range; and
   applying the amplitude modulated signal to the tissue to alter a function of the tissue without heating the tissue to temperatures lethal to the tissue.

2. The method of claim 1 wherein applying the amplitude modulated signal to the tissue comprises engaging the tissue with an electrode and coupling the electrode with a signal generator generating the amplitude modulated signal.

3. The method of claim 2 wherein engaging the tissue with an electrode comprises percutaneously placing the electrode in the patient's spinal cord.

4. The method of claim 2 wherein engaging the tissue with an electrode comprises percutaneously placing the electrode adjacent the patient's spinal cord.

5. The method of claim 2 wherein engaging the tissue with an electrode comprises percutaneously placing the electrode in epidural space near the patient's spinal cord.

6. The method of claim 2 wherein engaging the tissue with an electrode comprises percutaneously placing the electrode in joints between bones of the patient, the tissue being located in the joints.

7. The method of claim 2 wherein engaging the tissue with an electrode comprises placing the electrode near or in contact with nerves of the patient's teeth.

8. The method of claim 2 wherein engaging the tissue with an electrode comprises placing the electrode in the patient's brain.

9. The method of claim 8 wherein the electrode has a rigid shaft and wherein placing the electrode in the patient's brain comprises stereotactically inserting the electrode in the brain using a stereotactic aiming device.

10. The method of claim 2 further comprising implanting the signal generator in the patient's body.

11. The method of claim 10 wherein the signal generator is battery powered.

12. The method of claims 10 wherein the signal generator is powered by induction from a power source external to the body.

13. The method of claim 1 wherein temperatures lethal to the tissue are greater than 45° C.

14. The method of claim 1 wherein the at least one frequency component has a frequency greater than 300 Hz.

15. The method of claim 1 wherein altering the function of the tissue causes the patient to experience a reduction in pain.

16. The method of claim 1 wherein altering the function of the tissue causes the patient to experience a reduction in symptoms of epilepsy.

17. The method of claim 1 wherein altering the function of the tissue causes the patient to experience a reduction in pain by tremor.

18. The method of claim 1 wherein altering the function of the tissue causes the patient to experience a reduction in pain by symptoms of Parkinson's disease.

19. The method of claim 1 wherein altering the function of the tissue causes the patient to experience a reduction in symptoms of spasticity.

20. The method of claim 1 wherein altering the function of the tissue causes the patient to experience a reduction in symptoms of mood disorder.

21. The method of claim 1 wherein altering the function of the tissue causes the patient to experience a reduction in cardiac arrhythmia.

22. The method of claim 1 wherein altering the function of the tissue causes the patient to experience a reduction in pain associated with a neurological disorder of the patient's brain.

23. The method of claim 1 wherein the at least one frequency component alters the function of the tissue.

24. The method of claim 1 wherein the method provides sustained alteration of the function of the tissue even after application of the amplitude modulated signal ceases.

25. An apparatus for altering a function of tissue in a patient comprising:
   an electrode adapted to apply a signal to the tissue; and
   a signal generator coupled to the electrode, the signal generator adapted to generate an amplitude modulated signal having at least one frequency component above a physiologic stimulation frequency range, wherein application of the amplitude modulated signal to the tissue alters a function of the tissue while inhibiting heating of the tissue to temperatures lethal to the tissue.

26. The apparatus of claim 25 wherein altering the function of the tissue causes the patient to experience a reduction in pain.

27. The apparatus of claim 25 wherein altering the function of the tissue causes the patient to experience a reduction in symptoms of epilepsy.

28. The apparatus of claim 25 wherein altering the function of the tissue causes the patient to experience a reduction in pain by tremor.

29. The apparatus of claim 25 wherein altering the function of the tissue causes the patient to experience a reduction in pain by symptoms of Parkinson's disease.

30. The apparatus of claim 25 wherein altering the function of the tissue causes the patient to experience a reduction in symptoms of spasticity.

31. The apparatus of claim 25 wherein altering the function of the tissue causes the patient to experience a reduction in symptoms of mood disorder.

32. The apparatus of claim 25 wherein altering the function of the tissue causes the patient to experience a reduction in cardiac arrhythmia.

33. The apparatus of claim 25 wherein altering the function of the tissue causes the patient to experience a reduction in pain associated with a neurological disorder of the patient's brain.

34. The apparatus of claim 25 wherein the electrode is adapted to be inserted into the brain of the patient.

35. The apparatus of claim 25 wherein the electrode has a rigid shaft adapted to be stereotactically inserted in the brain of the patient using a stereotactic aiming device.

36. The apparatus of claim 25 wherein the electrode is flexible.

37. The apparatus of claim 25 wherein the electrode is a catheter-type electrode adapted for percutaneous placement.

38. The apparatus of claim 25 wherein the signal generator is adapted to be implanted in the body.

39. The apparatus of claim 38 wherein the signal generator is powered by a battery implanted in the body.

40. The apparatus of claims 38 wherein the signal generator is powered by an induction coupler to a power source external to the body.

41. The apparatus of claim 25 wherein the at least one frequency component causes alteration of a tissue function.

42. The apparatus of claims 25 wherein sustained alteration of a tissue function is provided even after application of the amplitude modulated signal ceases.

43. A method of causing a patient to experience a reduction in cardiac arrhythmia by altering a function of the patient's cardiac tissue, said method comprising applying an amplitude modulated signal to the cardiac tissue, said amplitude modulated signal having at least one frequency component above a physiologic stimulation frequency range to alter a function of the tissue causing the patient to experience a reduction in cardiac arrhythmia and pain, without raising the temperature of the cardiac tissue to levels lethal to the cardiac tissue.

44. A method of altering a function of neural tissue in the spinal cord of a patient comprising:

percutaneously placing an electrode in the spinal cord of the patient;

using a signal generator to generate an amplitude modulated signal having at least one frequency component above a physiologic stimulating frequency range, the at least one frequency component adapted to produce an alteration of the function of the neural tissue in the spinal cord of the patient, the alteration causing the patient to experience a reduction in pain, while producing an average power deposition in the neural tissue corresponding to non-lethal temperature elevation of the neural tissue in the spinal cord when the amplitude modulated signal is applied to the neural tissue through the electrode; and transmitting the amplitude modulating signal from the signal generator to the electrode.

45. A method of altering a function of tissue in joints between bones of a patient comprising:

inserting an electrode percutaneously into the joints between bones of the patient and in contact with tissue in the joints;

generating an amplitude modulated signal having at least one frequency component above a physiologic stimulation frequency range, the at least one frequency component adapted to alter the tissue in the joints between the bones, the alteration causing the patient to experience a reduction of pain, while producing the average power deposition in the tissue between the joints corresponding to non-lethal temperature elevation of the tissue in the joints when the amplitude modulated signal is applied to the tissue between the joints through the electrode; and transmitting the amplitude modulated signal to the electrode.

46. A method for reducing pain originating from nerves in a patient's teeth comprising:

placing an electrode near the nerves;

generating an amplitude modulated signal having at least one frequency component above a physiologic stimulating frequency range, the at least one frequency component adapted to alter a function of the nerves, the alteration causing the patient to experience a reduction in pain originating from the nerves, while producing an average power deposition in the nerves corresponding to non-lethal temperature elevation of the nerves when the amplitude modulated signal is applied to the nerves through the electrode; and transmitting the signal to the electrode.

* * * * *